United States Patent [19]
Bózsing et al.

[11] Patent Number: 6,046,337
[45] Date of Patent: Apr. 4, 2000

[54] PROCESS FOR THE PREPARATION OF A DIHYDROPYRIDINE DERIVATIVE

[75] Inventors: Dániel Bózsing; Györgyi Lax Kovány; Gyula Simig; György Krasznai; Gábor Blaskó ; Péter Tömpe; Kálman Nagy; Györgyi Donáth Vereczkey; Gábor Némei; Norbert Németh, all of Budapest, Hungary

[73] Assignee: EGIS Gyogyszergyar Rt., Budapest, Hungary

[21] Appl. No.: 09/133,108

[22] Filed: Aug. 12, 1998

[30] Foreign Application Priority Data

Aug. 12, 1997 [HU] Hungary ................................. 9701379

[51] Int. Cl.[7] .................................................. C07D 211/86
[52] U.S. Cl. ........................................... 546/321; 514/356
[58] Field of Search ............................................... 546/321

[56] References Cited

U.S. PATENT DOCUMENTS

| | | | |
|---|---|---|---|
| 4,879,303 | 11/1989 | Davison et al. | 514/356 |
| 5,001,119 | 3/1991 | Schartz et al. | 514/177 |
| 5,438,145 | 8/1995 | Furlan et al. | 546/321 |

*Primary Examiner*—Jane Fan
*Attorney, Agent, or Firm*—Smith, Gambrell & Russell, LLP

[57] ABSTRACT

The invention relates to a new process for the preparation of amlodipine besylate of the Formula

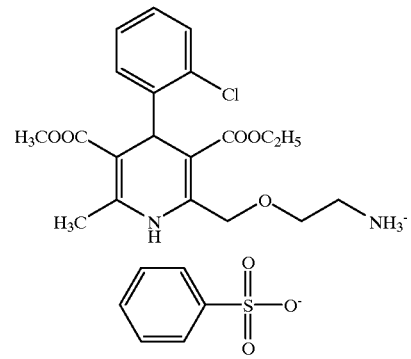

(I)

Amlodipine besylate of the Formula I is a valuable known blood pressure decreasing antianginal agent.

The advantage of the process of the present invention is that it can be carried out in a simple way with high yields and there is no need to isolate the amlodipine base.

22 Claims, No Drawings

PROCESS FOR THE PREPARATION OF A DIHYDROPYRIDINE DERIVATIVE

The present invention relates to a new process for the preparation of 3-ethyl-5-methyl-2-(2-aminoethoxy-methyl)-4-(2-chloro-phenyl)-6-methyl-1,4-dihydro-3,5-pyridine-dicarboxylate benzenesulfonic acid. This compound is a known pharmaceutical active ingredient having the INN amlodipine besylate.

Amlodipine besylate is a calcium antagonist of the dihydropyridine-dicarboxylate type and possesses valuable strong long-lasting blood pressure decreasing and antianginal properties.

According to the known procedures the dihydropyridine structure of amlodipine is built up by means of the Hantzsch synthesis suggested by prior art for reactions of this type. The main feature of the process disclosed in EP 89,167 and HU 186,868 is that the primary amino group is formed in the last step of the synthesis either by removing the protecting group from a protected amino group or by reducing the corresponding azide. The protected amino group or the azido group is introduced into the molecule by incorporating into the acetoacetate component of the Hantzsch synthesis.

According to the first process mentioned above in the Hantzsch synthesis a 4-(2-aminoethoxy)-acetoacetic ester bearing a protected amino group, 2-chloro-benzaldehyde and an amino crotonic acid ester are reacted, or in a variant of said process a 4-(2-aminoethoxy)-acetoacetate is condensed first with a 2-chloro-benzaldehyde and the "ylidine" derivative thus obtained is reacted with an amino crotonic acid ester. Amlodipine is prepared by removing the protecting group from the dihydropyridine derivative containing a protected primary amino group obtained in the Hantzsch synthesis.

According to the other process referred to Hantzsch synthesis is performed by reacting a 4-(2-azidoethoxy)-acetoacetic acid ester, 2-chloro-benzaldehyde and amino crotonic acid ester. The primary amino group of amlodipine is formed by reducing the azido group.

In the EP cited above pharmaceutically acceptable acid addition salts of amlodipine are disclosed. Said salts are prepared from amlodipine by salt formation. Among the salts the maleate is described as the most advantageous one.

The disadvantage of the above procedures is the relatively low yield of the individual reaction steps (the yield of the Hantzsch synthesis is not even disclosed). It is known further on that the azide is explosive (see citation C.A. 105, 11321t relating to the relevant azido compound).

According to DE 3,710,457 the benzenesulfonic acid salt of amlodipine and a process for the preparation thereof is disclosed. According to this patent specification said salt exhibits numerous advantages over other known salts of amlodipine, particularly in the conversion of the salt into pharmaceutical compositions. Amlodipine besylate is prepared by reacting amlodipine base with a solution of benzenesulfonic acid or the ammonium salt thereof formed with an inert solvent and isolating the amlodipine besylate thus obtained from the reaction mixture.

In EP 599,220 a new process for the preparation of amlodipine besylate is disclosed. An amlodipine derivative containing a trityl protective group on the primary amino group is prepared by using the conventional Hantzsch synthesis. The protecting trityl group is removed by hydrolysis carried out in the presence of benzenesulfonic acid. Thus amlodipine besylate is obtained without isolating the amiodipine base. The significant drawback of this process resides in the low yield. It is a further important disadvantage that pure end-product can only be obtained with the aid of extremely complicated measures. The overall yield is only 7%, related to 2-chloro-benzaldehyde.

It is the object of the present invention to overcome the above disadvantages of the known procedures and to provide a process which enables the preparation of amlodipine besylate with high yields, can be carried out in a simple way and eliminates the isolation of amlodipine base.

The above object is achieved with the aid of the process of the present invention.

According to the present invention there is provided a process for the preparation of 3-ethyl-5-methyl-2-(2-aminoethoxy-methyl)4-(2-chloro-phenyl)-6-methyl-1,4-dihydro-3,5-pyridine-dicarboxylate benzenesulfonic acid salt of the Formula

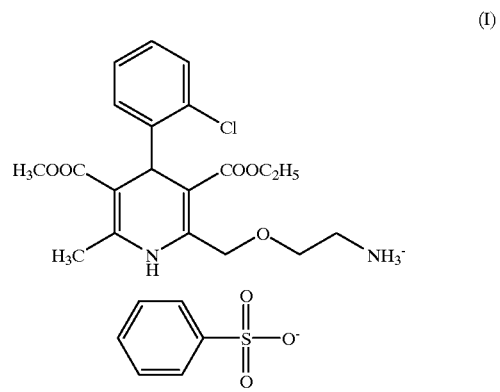

(I)

which comprises $a_1$) reacting the compound of the Formula

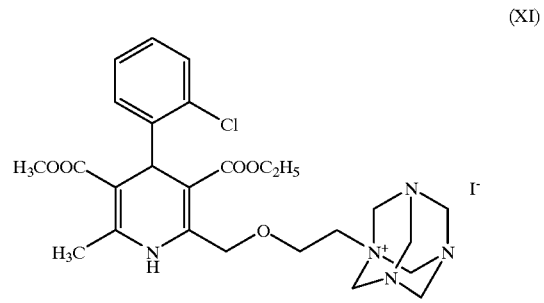

(XI)

with benzenesulfonic acid of the Formula

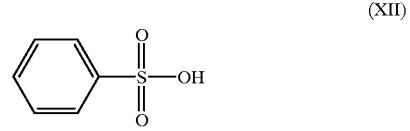

(XII)

or a₂) reacting the compound of the Formula (IX)

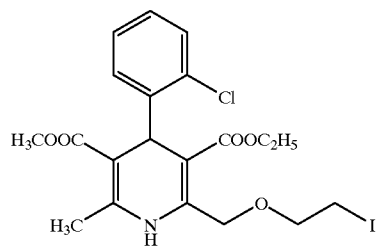

with hexamethylene tetramine of the Formula (X)

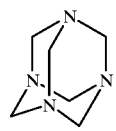

and reacting the compound of the Formula XI thus obtained with benzenesulfonic acid of the Formula XII; or a₃) exchanging in a compound of the Formula (VIII)

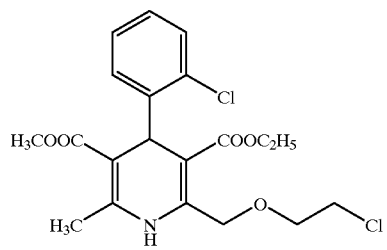

the chlorine for iodine, reacting the compound of the Formula IX thus obtained with hexamethylene tetramine of the Formula X and reacting the compound of the Formula XI thus obtained with benzenesulfonic acid of the Formula XII; or a₄) reacting the compound of the Formula (VI)

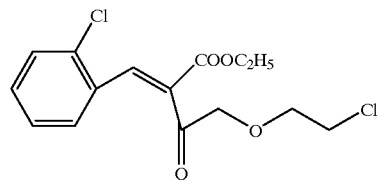

with methyl-3-amino crotonate of the Formula (VII)

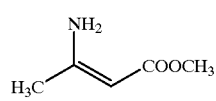

exchanging in the compound of the Formula VIII thus obtained the chlorine for iodine, reacting the compound of the Formula IX thus obtained with hexamethylene tetramine of the Formula X and reacting the compound of the Formula XI thus obtained with benzenesulfonic acid of the Formula XII; or a₅) reacting the compound of the Formula (IV)

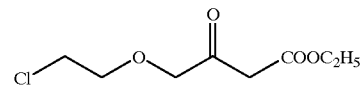

with 2-chloro-benzaldehyde of the Formula (V)

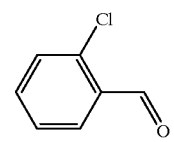

reacting the compound of the Formula VI thus obtained with methyl-3-amino-crotonate of the Formula VII, exchanging in the compound of the Formula VIII thus obtained the chlorine for iodine, reacting the compound of the Formula IX thus obtained with hexamethylene tetramine of the Formula X and reacting the compound of the Formula XI thus obtained with benzenesulfonic acid of the Formula XII; or a₆) reacting ethyl-4-bromo-acetoacetate of the Formula (II)

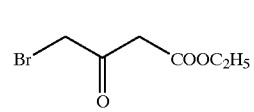

with ethylene chlorohydrine of the Formula (III)

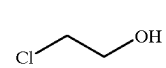

reacting the compound of the Formula IV thus obtained with 2-chloro benzaldehyde of the Formula V, reacting the compound of the Formula VI thus obtained with methyl-3-amino-crotonate of the Formula VII, exchanging in the compound of the Formula VIII thus obtained the chlorine for iodine, reacting the compound of the Formula IX thus obtained with hexamethylene tetramine of the Formula X and reacting the compound of the Formula XI thus obtained with benzenesulfonic acid of the Formula XII; or a₇) exchanging in the compound of the Formula IV the chlorine for iodine, reacting the compound of the Formula (XIII)

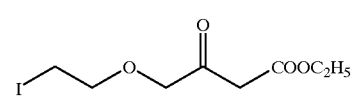

thus obtained with 2-chloro-benzaldehyde of the Formula V, reacting the compound of the Formula

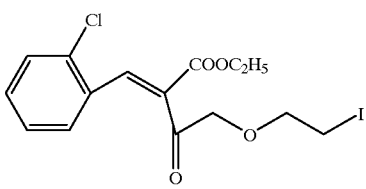
(XIV)

thus obtained with methyl-3-amino-crotonate of the Formula VII, reacting the compound of the Formula IX thus obtained with hexamethylene tetramine of the Formula X and reacting the compound of the Formula XI thus obtained with benzenesulfonic acid of the Formula XII.

The essential feature of our invention is that in the Hantzsch synthesis the benzylidene derivative of the Formula VI prepared from ethyl 4-(2-chloroethoxy)-acetoacetate of the Formula IV and 2-chloro-benzaldehyde of the Formula V is reacted with the amino crotonic acid ester of the Formula VII whereby the new 2-chloroethoxy-dihydropyridine derivative of the Formula VIII and after chlorine→iodine exchange the new 2-iodoethoxy-dihydropyridine derivative of the Formula IX is obtained with good yields.

The compounds of the Formulae VIII and IX are new, not described in prior art. In this way amlodipine besylate is prepared by a new and very advantageous method by ammonolysis of the halogeno derivative by means of the so-called Delepine reaction. The halogen is replaced by the amino group by using hexamethylene tetramine as ammonia source. The urotropine salt formed is decomposed by using benzenesulfonic acid whereby amlodipine besylate is directly isolated from the reaction mixture. The latter process is new, not disclosed in prior art.

According to the process of the present invention—contrary to methods described in prior art—the primary amino group is not built up by introducing into the molecule as part of the acetoacetic acid ester component in protected form and subsequently removing the protecting group of the amino group but rather by a halogen→amine exchange reaction carried out after the Hantzsch reaction performed by using the corresponding halogeno compound. According to a characteristic essential element of the process of the present invention the latter reaction is carried out in a manner not disclosed in prior art whereby in the reaction not amlodipine base but directly the desired besylate salt is formed. The process is shown on the reaction scheme.

According to the first step of the process of the present invention ethylene chlorohydrine of the Formula III (2-chloro-ethanol) is O-alkylated with ethyl-4-bromo-acetoacetate of the Formula II. The compound of the Formula IV thus obtained is new. The process is carried out in a known manner. The reaction is performed in a suitable inert solvent, preferably an aliphatic or alicyclic ether, particularly in tetrahydrofurane at a temperature of about −10° C. or below said temperature. The hydrogen bromide formed is bound with a basic substance preferably with sodium hydride, which can be used in the form of an oily suspension or can be made previously free of paraffine. The reaction mixture may be worked up in a known manner by decomposing with an acid, neutralization and extraction. The pure product may be obtained by fractionated distillation in vacuo.

According to the next step of the synthesis the chloroethoxy-acetoacetic acid ester of the Formula IV is subjected to aldol condensation with 2-chloro-benzaldehyde of the Formula V. As reaction product the "ylidene" derivative of the Formula VI is obtained. The reaction of the aldehyde and the acetoacetic acid derivative may be preferably carried out in the presence of a catalytic amount of piperidine acetate, whereby the ethyl 2-chloro-benzylidene-4-chloroethoxy-acetoacetate of the Formula VI is obtained with very high yield. The piperidine acetate catalyst is preferably used in a 0.01-0.1 molar amount, related to 1 mole of the compound of the Formula IV. As reaction medium polar protic solvents may be used, preferably alkanols, particularly isopropanol. The reaction temperature is between 10° C. and 60° C., one may preferably work at room temperature. The reaction time varies between 5 and 15 hours and is preferably 10 hours. The reaction mixture may be worked up by evaporating the solvent and washing with water. The crude product thus obtained is generally suitable for further chemical transformation.

One may also proceed by subjecting the compound of the Formula VI to further chemical reaction directly, without isolation, in the solvent used.

According to the next step of the synthesis the compound of the Formula VIII is prepared by Hantzsch synthesis. One may generally proceed by heating to boiling the benzylidene derivative of the Formula VI and the amino crotonate of the Formula VII in a suitable organic solvent. As reaction medium preferably a $C_{1-4}$ alkanol (particularly isopropanol, methanol or ethanol) or a polar aprotic solvent (e.g. acetonitrile) or a mixture thereof may be used.

One may also proceed by reacting 2-chloro-benzaldehyde of the Formula V, the keto ester of the Formula IV and the amino crotonate of the Formula VII without isolating the benzylidene derivative of the Formula VI until the reaction becomes complete. The reaction time is 15–20 hours or shorter. The reaction mixture is worked up in a known manner (e.g. cooling and filtration).

In the next step the compound of the Formula VIII is converted into the compound of the Formula IX. The chlorine is exchanged for iodine by the "Finkelstein reaction" known from prior art per se. The reaction may be preferably carried out with an alkali iodide, particularly sodium iodide. According to the teaching of prior art this reaction is carried out preferably in acetone in view of the solubility conditions. The process of the present invention may be performed in acetone but the use of alkanols having a high boiling point (particularly isopropanol) proved to be particularly advantageous. The reaction may be carried out under heating, preferably at the boiling point of the reaction mixture. The reaction time is generally 20–25 hours or shorter. The reaction mixture may be worked up in a known manner (e.g. filtration after intensive cooling). The dihydropyridine derivative of the Formula IX is obtained with good yields.

According to an alternative embodiment of the process of the present invention the chlorine→iodine exchange is carried out at the stage of the chloroethoxy acetoacetate of the Formula IV. This reaction gives the lodo-acetoacetate of the Formula XIII. The reaction is preferably carried out in acetone as medium at the boiling point of the reaction mixture. The product may be purified by fractionated distillation. The compound of the Formula XIII thus obtained is converted into the benzylidene derivative of the Formula XIV by reaction with 2-chloro-benzaldehyde of the Formula V. This reaction is carried out as described above in connection with the reaction of the compounds of the Formulae IV and V. The compound of the Formula XIV thus obtained is reacted with the compound of the Formula VII to yield the iodoethoxy-dihydropyridine derivative of the Formula IX. Said reaction is performed in an analogous manner to the Hantzsch reaction earlier described.

According to the next step of the process of the present invention a quaternary salt is formed from the iodo derivative of the Formula IX—being more reactive than the chloroethoxy-dihydropyridine of the Formula VIII—by reaction with hexamethylene tetramine (urotropine) of the Formula X. According to the teaching of prior art salts of such type are generally prepared in apolar-aprotic solvents. It has been found, however, that the reaction of the compounds of the Formulae IX and X may be carried out more advantageously by using a lower alkanol (e.g. methanol, ethanol, isopropanol) or acetonitrile as reaction medium. One may work particularly preferably in acetonitrile as medium. The reactants may be used in equimolar amount, but urotropine of the Formula X may also be used preferably in an excess of 10–15%. The reaction may be carried out at a temperature between room temperature and the boiling point of the solvent, preferably at 40–55° C. One may proceed by adding the reaction components simultaneously to the solvent or adding the iodo compound of the Formula IX to the solution of hexamethylene tetramine preferably in small portions. The reaction time is 20–50 hours, preferably 30–40 hours. The dihydropyridine—urotropine quaternary salt of the Formula XI precipitates as a solid and can be simply filtered off at room temperature. The crude product is of a purity suitable for the preparation of the end-product and no further purification is required.

According to the next step amlodipine besylate of the Formula I is prepared by subjecting the quaternary salt of the Formula XI to hydrolysis with benzenesulfonic acid of the Formula XII.

Hydrolysis with benzenesulfonic acid is carried out in a mixture of water and an organic solvent. For this purpose organic solvents can be used which are water-miscible or partially miscible or immiscible with water. As water miscible organic solvent preferably straight or branched chained alkanols having 1–3 carbon atoms may be used (e.g. methanol, ethanol, isopropanol). As organic solvents partially miscible or immiscible with water preferably alkanols having 4–8 carbon atoms (e.g. n-butanol) or ethyl acetate may be used. The reaction may be carried out at a temperature between room temperature and the boiling point of the solvent; one may preferably work at the boiling point of the reaction mixture. Benzenesulfonic acid may be preferably used in at least a 4 molar amount related to the compound of the Formula XI. For practical reasons it is preferred to use not more than 10 molar equivalents of benzenesulfonic acid. According to a particularly preferred embodiment of the process the reaction is carried out by using about 5 molar equivalents of benzenesulfonic acid. The reaction mixture may be worked up in a manner known per se.

The starting materials of the Formulae III, V, X and XII are commercially available. The bromo acetoacetate of the Formula II is a known compound and can be prepared e.g. according to U.S. Pat. No. 3,786,082 and EP 102,893. The amino crotonate of the Formula VI is known as well (HU 202,474).

The intermediates of the Formulae IV, VI, VIII, IX, XI, XIII and XIV are new compounds, not disclosed in prior art.

According to a further aspect of the present invention there are provided new compounds of the Formulae IV, VI, VIII, IX, XI, XIII and XIV and a process for the preparation thereof.

Compounds of the dihydropyridine dicarboxylate structure are mixed esters and contain an asymmetrical center. Such compounds may occur in the form a pair of enantiomers, which can be separated by methods well-known from prior art. The present invention encompasses the individual isomers (dextro and laevo rotatory isomers) and mixtures thereof (including racemic mixtures).

According to the process of the present invention the desired compound of the Formula I may be obtained via new intermediates not described in prior art. The hydrolysis of the quaternary salt of the Formula XI with benzenesulfonic acid is a new process.

The advantage of the process of the present invention is that the yields of the individual steps are high. The yield of the Hantzsch cyclisation step used in the invention process is higher than that of the known cyclisation reactions leading to amlodipine. A further advantage of the invention process resides in the fact that there is no need to isolate the base because the precipitated salt is directly formed in one step. The process is feasible on industrial scale too, no special equipment is required.

Further details of the present invention are to be found in the following Examples without limiting the scope of protection to said Examples.

EXAMPLE 1

Ethyl-4-(2-chloroethoxy)-acetoacetate (IV)

10.38 g (0.25 mole) of 57.8% sodium hydride are added to 110 ml of tetrahydrofurane. The mixture is cooled to a temperature between −10° C. and −20° C. whereupon at this temperature 10.08 g (0.125 mole) of ethylene chlorohydrine (III) are added under nitrogen dropwise. The mixture is stirred for 20 minutes, whereupon at the same temperature a solution of 26.18 g (0.125 mole) of ethyl-4-bromoacetoacetate (II) and 35 ml of tetrahydrofurane is added. The reaction mixture is stirred for 20 minutes, allowed to warm to room temperature, kept at this temperature for 6 hours, poured into 270 ml of 1 N hydrochloric acid under cooling and extracted with dichloro methane. The organic layer is dried and evaporated. The residual oil is made free of paraffine by treatment with a 1:1 mixture of acetonitrile and benzene. The product is distilled off in vacuo. Thus 17.47 g of the desired compound are obtained, yield 67%, bp.: 110° C./2 Hgmm.

Elementary analysis: for the Formula $C_8H_{13}ClO_4$ (208.41) calc.: C 46.05%, H 6,28%, Cl 16.99% found: C 46.45%, H 6.11%, Cl 16.52%

EXAMPLE 2

Ethyl-4-(2-iodoethoxy)-acetoacetate (XIII)

To a solution of 19 g (91 millimoles) of ethyl-4-(2-chloroethoxy)-acetoacetate (IV) and 380 ml of acetone 134.4 g (910 millimoles) of sodium iodide are added. The reaction mixture is heated to boiling for 13 hours. The inorganic substance is filtered off and the filtrate is evaporated in vacuo. The residual oil is dissolved in dichloro methane, the solution is washed with water, dried and evaporated. The crude product is subjected to fractionated distillation in vacuo. Bp.: 170° C./0.1 Hgmm. Thus 18.3 g of the desired product are obtained, yield 67%.

Elementary analysis: for the Formula $C_8H_{13}IO_4$ (300.091) caic: C 32.02%, H 4.37% found: C 31.86%, H 4.36%

EXAMPLE 3

Ethyl-4-(2-chloroethoxy)-2-(2-chlorobenzylidene)-acetoacetate (VI)

16.64 g (0.118 mole) of 2-chloro-benzaldehyde (V) and 24.7 g (0.118 mole) of ethyl-4-(2-chloroethoxy)-acetoacetate (IV) are reacted in 365 ml of isopropanol in the presence of a piperidine acetate catalyst [10 g (11.8 millimoles) of piperidine+0.7 g (11.8 millimoles) of acetic acid] at room temperature for 10 hours. The reaction mixture is evaporated, the residual oil is dissolved in dichloro methane, washed with water and dried. The organic phase is evaporated in vacuo. Thus 37.9 g of the desired product are obtained in the form of a yellow oil, yield 97%.

Elementary analysis: for the Formula $C_{15}H_{16}Cl_2O_4$ (331.203) calc.; C 54.39%, H 4.87%, Cl 21.41% found: C 53.69%, H 5.03%, Cl 20.98%

EXAMPLE 4

Ethyl-4-(2-iodo-ethoxy)-2-(2-chloro-benzylidene)-acetoacetate (XIV)

10 g (33 millimoles) of ethyl-4-(2-iodoethoxy)-acetoacetate (XIII) and 4.64 g (33 millimoles) of 2-chloro-benzaldehyde (V) are reacted in 100 ml of isopropanol in the presence of a piperidine acetate catalyst [0.28 g (3.3 millimoles) of piperidine+0.198 g (3.3 millimoles) of acetic acid] at room temperature for 10 hours. The reaction mixture is evaporated, the residual oil dissolved in dichloro methane, washed with water and dried. The organic phase is evaporated in vacuo. Thus 11.55 g of the desired product are obtained in the form of a reddish brown oil, yield 83%.

Elementary analysis: for the Formula $C_{15}H_{16}ClIO_4$ (422.643) calc.: C 42.63%, H 3.82%, Cl 8.39% found: C 43.00%, H 4.12%, Cl 8.13%

EXAMPLE 5

3-ethyl-5-methyl-2-(2-chloro-ethoxy-methyl)-4-(2-chloro-phenyl)-6-methyl-1,4-dihydro-3,5-pyridine-dicarboxylate (VIII)

A mixture of 36 g (0.1087 mole) of ethyl-4-(2-chloro-ethoxy)-2-(2-chloro-benzylidene)-acetoacetate (VI) and 12.5 g (0.1087 mole) of methyl-3-amino-crotonate (VII) in 335 ml of isopropanol is reacted at the boiling point of the reaction mixture for 20 hours. The reaction mixture is cooled to a temperature between 0° C. and −5° C. and allowed to stand in a refrigerator overnight. Next morning the precipitate is filtered, washed successively with cold isopropanol and diisopropyl ether. The crude product may be recrystallized from diisopropyl ether or aqueous acetic acid, if necessary. Thus 21.88 g of the desired product are obtained, yield 47%, mp.: 152–154° C.

Elementary analysis: for the Formula $C_{20}H_{23}Cl_2NO_5$ (428.32) calc.: C 56.08%, H 5.41%, N 3.27%, Cl 16.56% found: C 56.10% H 5.42%, N 3.37%, Cl 16.18%

EXAMPLE 6

3-ethyl-5-methyl-2-(2-iodoethoxy)-methyl-4-(2-chloro-phenyl)-6-methyl-1,4-dihydro-3,5-pyridine-dicarboxylate (IX)

Method a)

A mixture of 16 g (37 millimoles) of 3-ethyl-5-methyl-2-(2-chloro-ethoxy-methyl)-4-(2-chloro-phenyl)-6-methyl-1,4-dihydro-3,5-pyridine-dicarboxylate (VIII), 55.46 g (370 millimoles) of sodium iodide and 183 ml of isopropanol is stirred under boiling for 20 hours. The reaction mixture is cooled to a temperature between 0° C. and −5° C. and stored in a refrigerator overnight. Next morning the precipitate is filtered off and washed with cold isopropanol. The crude product is recrystallized from isopropanol. Thus 16.35 g of the desired compound are obtained, yield 85%, mp: 152–154° C.

Elementary analysis: for the Formula $C_{20}H_{23}Cl\ INO_5$ (519.76) calc.: C 46.22%, H 4,46%, N 2.69% Cl 6.82% found: C 45.92%, H 4.45%, N 2.73%, Cl 6.77%

Method b) A mixture o f 11 g (2 6 millimoles) of ethyl-4-(2-iodo-etho xy)-2-(2-chloro-benzylidene)-acetoacetate (XIV), 2.99 g (26 millimoles) of methyl-3-amino-crotonate (VII) and 110 ml of isopropanol is heated to boiling for 8 hours. The reaction mixture is evaporated, the residue crystallized from cold isopropanol, filtered and washed with cold isopropanol. The crude product is recrystallized from isopropanol. Thus 2.97 g of the desired compound are obtained, yield 22%, mp: 152–155° C.

EXAMPLE 7

3-ethyl-5-methyl-2-(2-yy-ethoxy-methyl)-4-(2-chloro-phenyl)-6-methyl-1,4-dihydro-3,5-pyrdine-dicarboxylate-hexaminium iodide (XI)

1.77 g (12.7 millimoles) of hexamethylene tetramine (X) are added to 15 ml of acetonitrile. The mixture is stirred at room temperature for 10 minutes, warmed to 45–50° C., whereupon 6.0 g (11.5 millimoles) of 3-ethyl -5-methyl-2-(2-iodo-ethoxy)-methyla-(2-chloro-phenyl),6-methyl-1,4-dihydro-3,5-pyridine-dicarboxylate (IX) are added in small portions within about 2 hours. The reaction mixture is stirred at this temperature for 40 hours, allowed to cool to room temperature, filtered and washed successively with acetonitrile and dichloro methane. Thus 6.83 of the desired product are obtained in the form of a white powder, yield 90%, mp.: 177–179° C.

Elementary analysis: for the Formula $C_{26}H_{35}Cl\ IN_5O_5$ (659.957) calc.: C 47.32%, H 3,35%, N 10.61% found: C 46.84%, H 5.42%, N 10.40%

EXAMPLE 8

3-ethyl-5-methyl-2-(2-aminoethoxy-methyl)-4-(2-chloro-phenyl)-6-methyl-1,4-dihydro-3,5-pyridine-dicarboxylate benzenesulfonic acid salt (amlodipine bezylate) (I)

Method a)

A mixture of 3.3 g (5 millimoles) of 3-ethyl-5-methyl-2-(2-yl-ethoxy-methyl)-4-(2-chloro-phenyl)-6-methyl-1,4-dihydro-3,5-pyridine-dicarboxylate-hexaminium iodide (XI), 3.95 g (25 millimoles) of benzenesulfonic acid (XII), 350 ml of n-butanol and 350 ml of water is heated to boiling under vigorous stirring for 45 minutes. The reaction mixture is allowed to cool to room temperature and the layers are separated. The organic layer is washed with water, dried and evaporated.

The residual oil is crystallized by storing in cold ethyl acetate in a refrigerator overnight. Next morning the crystalline product is filtered off, washed with ethyl acetate and dried. The dry product is thoroughly washed with water, dried and recrystallized from acetonitrile. Thus 1.5 g of amlodipine besylate are obtained, yield 52.9%, mp.: 202–203° C.

Method b)

A mixture of 8.8 g (0.013 mole) of 3-ethyl-5-methyl-2-(2-yl-ethoxy-methyl)-4-(2-chloro-phenyl)-6-methyl-1,4-dihydro-3,5-pyridine-dicarboxylate-hexaminium iodide (XI), 10.54 g (0.066 mole) of benzenesulfonic acid (XII), 535 ml of methanol and 535 ml of water is refluxed for an hour. The reaction mixture is allowed to cool to room temperature, poured onto water, extracted with dichloro methane, washed with water, dried and evaporated. The residue is crystallized by storing in acetonitrile in a refrigerator overnight. Thus 4.18 g of amlodipine besylate are obtained, yield 55.4%, mp.: 205–206° C. (acetonitrile).

Elementary analysis: for the Formula $C_{26}H_{31}ClN_2O_8S$ (567.055) calc.: C 55.07%, H 5,51%, N 4.94%, Cl 6.25%, S 5.65% found: C 54.71%, H 5.53%, N 4.95% Cl 6.05%, S 5.57%

What we claim is:

1. A process for the preparation of 3-ethyl-5-methyl-2-(2-aminoethoxymethyl)-4-(2-chlorophenyl)-6-methyl-1,4-dihydro-3,5-pyridine-dicarboxylate benzenesulfonic acid salt of the formula

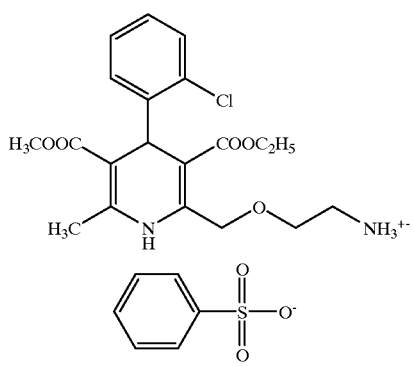

(I)

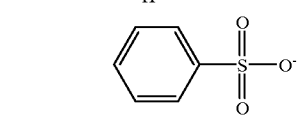

which comprises:

reacting the compound of the Formula

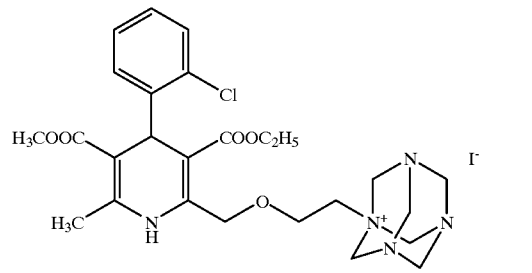

(XI)

with benzenesulfonic acid of the Formula

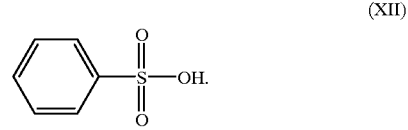

(XII)

2. The process according to claim 1, further comprising a preliminary step of producing the compound of the Formula

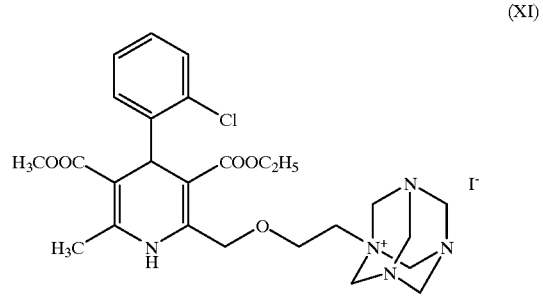

(XI)

by reacting the compound of the Formula

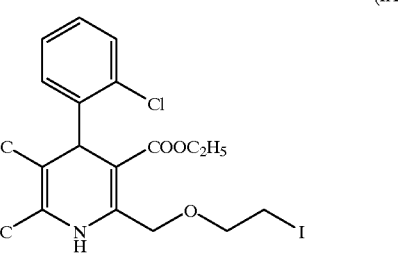

(IX)

with hexamethylene tetramine of the Formula

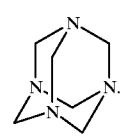

(X)

3. The process according to claim 2, further comprising a preliminary step of producing the compound of the Formula by exchanging in a compound of the Formula (IX)

chlorine for iodine.

4. The process according to claim 3, further comprising a preliminary step of producing the compound of the Formula (VIII)

by reacting the compound of the Formula (VI)

with methyl-3-amino crotonate of the Formula (VII)

5. The process according to claim 4, further comprising a preliminary step of producing the compound of the Formula by reacting the compound of the Formula (VI)

with 2-chloro-benzaldehyde of the Formula (IV)

(V)

6. The process according to claim 5, further comprising a preliminary step of producing the compound of the Formula (IV)

by reacting ethyl-4-bromo-acetoacetate of the Formula (II)

with ethylene chlorohydrine of the Formula (III)

7. The process according to claim 2, further comprising a preliminary step of producing the compound of the Formula (IX)

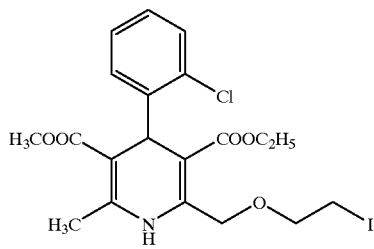

by replacing in the compound of the Formula (IV)

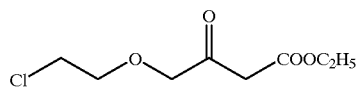

chlorine for iodine, reacting the compound of the Formula (XIII)

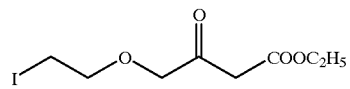

thus obtained with 2-chloro-benzaldehyde of the Formula (V)

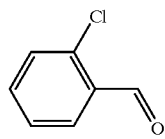

and
reacting the compound of the Formula (XIV)

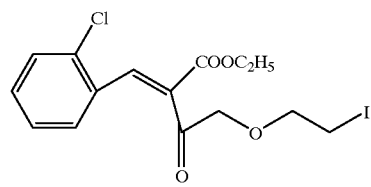

thus obtained with methyl-3-amino-crotonate of the Formula (VII)

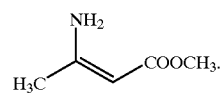

8. The process according to claim 1, wherein the reaction of the compound of Formula XI with benzenesulfonic acid of the Formula XII is a hydrolysis carried out in a mixture of water and an organic solvent.

9. The process according to claim 8, wherein the organic solvent is water miscible.

10. The process according to claim 9, wherein the water miscible organic solvent is an alkanol having 1–3 carbon atoms.

11. The process according to claim 8, wherein the organic solvent is partially miscible or immiscible with water.

12. The process according to claim 11, wherein the organic solvent is an alkanol having 4–8 carbon atoms, and being preferably one member selected from n-butanol and ethyl acetate.

13. The process according to claim 1, wherein benzenesulfonic acid is present in at least a 4 molar amount, and Formula XI is present in a 1 molar amount.

14. The process according to claim 2, wherein the reaction is carried out in a lower alkanol or acetonitrile.

15. The process according to claim 3, wherein the exchange of chlorine by iodine is performed by reaction Formula VIII with an alkali iodide, and preferably sodium iodide.

16. The process according to claim 15, wherein the reaction is carried out in an alkanol having a high boiling point, and preferably isopropanol.

17. The process according to claim 4, wherein the reaction of the compounds of the Formulas VI and VII is carried out in a solvent comprising at least one selected from an alcohol having 1–4 carbon atoms and a polar aprotic solvent.

18. The process according to claim 17, wherein the solvent is methanol.

19. The process according to claim 17, wherein the solvent is isopropanol.

20. The process according to claim 17, wherein the solvent is acetonitrile.

21. The process according to claim 5, wherein the reaction of the compounds of Formulas IV and V is carried out in the presence of piperidine acetate as a catalyst.

22. The process according to claim 7, wherein the exchange of iodine for chlorine in the compound of Formula IV is carried out by reaction Formula IV with an alkali iodide, preferably sodium iodide.

* * * * *